United States Patent [19]

Gonella

[11] 4,393,053
[45] Jul. 12, 1983

[54] THIOLIC DERIVATIVES OR ERYTHROMYCIN HAVING THERAPEUTIC ACTIVITY AND PHARMACEUTICAL COMPOSITIONS CONTAINING THEM

[75] Inventor: Jacques Gonella, Zollikon, Switzerland

[73] Assignee: Refarmed S.A., Zollikon, Switzerland

[21] Appl. No.: 344,961

[22] Filed: Feb. 2, 1982

[30] Foreign Application Priority Data

Feb. 2, 1981 [FR] France ............................. 82 00821

[51] Int. Cl.$^3$ ........................ A61K 31/71; C07H 17/08
[52] U.S. Cl. ..................... 424/180; 536/7.2; 536/7.3; 536/7.4
[58] Field of Search .................. 536/9, 7.2, 7.4, 7.3; 424/180

[56] References Cited

U.S. PATENT DOCUMENTS

| | | | |
|---|---|---|---|
| 2,653,899 | 9/1953 | Bunch et al. | 536/9 |
| 2,743,268 | 4/1956 | Stieff | 536/9 |
| 2,830,982 | 4/1958 | Stainbrook et al. | 536/9 |
| 3,558,594 | 1/1971 | Jones et al. | 536/9 |
| 3,847,896 | 11/1974 | Sinkula | 536/7.2 |
| 4,261,982 | 4/1981 | Luedders et al. | 536/9 |
| 4,264,765 | 4/1981 | Bodor et al. | 536/9 |

FOREIGN PATENT DOCUMENTS 44504 1/1982 European Pat. Off.
2018756 10/1979 United Kingdom.

OTHER PUBLICATIONS

Kikuchi et al., "Chem. Abst.", vol. 93, 1980, P38279f.
Labadarios et al., "Chem. Abst.", vol. 85, 1976, P153992(e).
Zanolo et al., "Chem. Abst.", vol. 95, 1981, P54571s.

*Primary Examiner*—Johnnie R. Brown
*Attorney, Agent, or Firm*—Cushman, Darby & Cushman

[57] ABSTRACT

The thiolic salts of erythromycin and of the propionic ester of erythromycin with thenoyl alpha-mercaptopropionylglycine find therapeutical use in the cases in which erythromycin or its propionic ester are used and are generally endowed with very low toxicity and high hematic levels.

7 Claims, 2 Drawing Figures

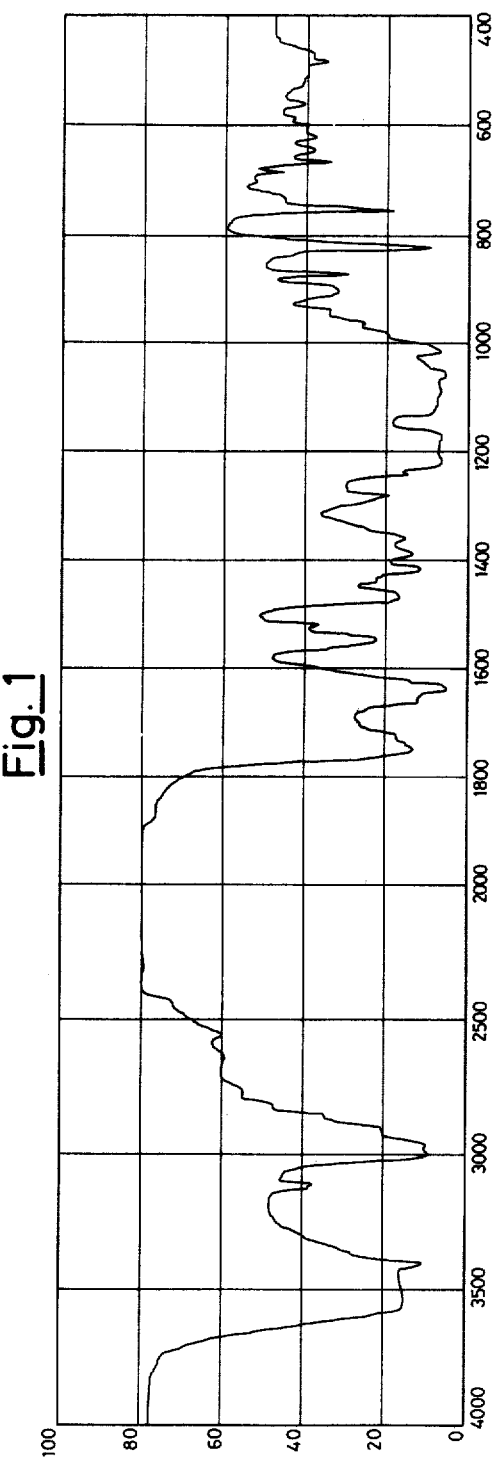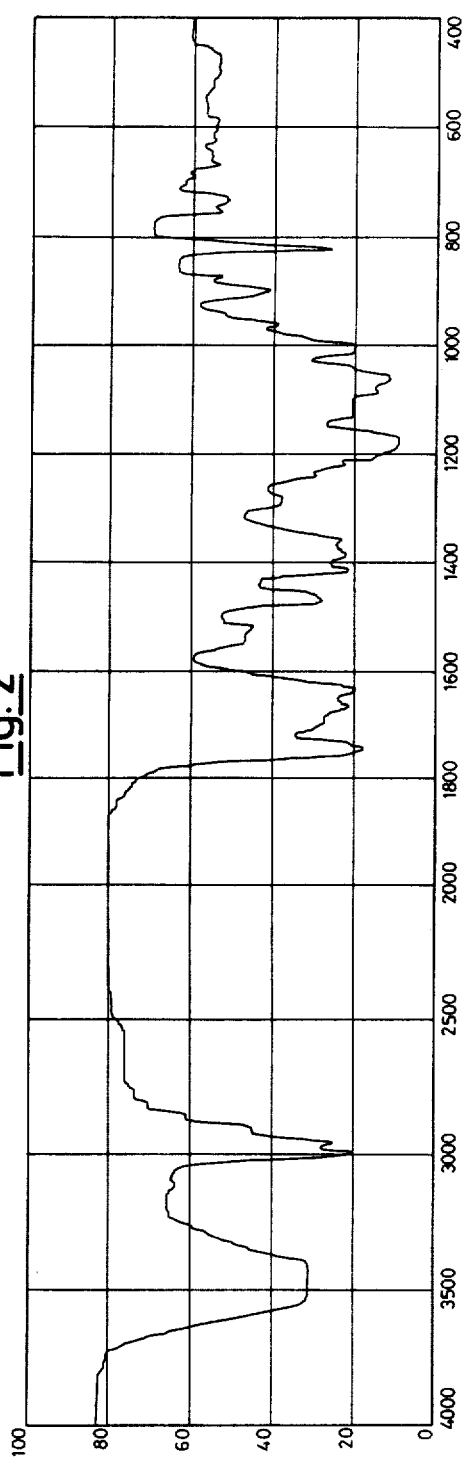

THIOLIC DERIVATIVES OR ERYTHROMYCIN HAVING THERAPEUTIC ACTIVITY AND PHARMACEUTICAL COMPOSITIONS CONTAINING THEM

The present invention relates to novel thiolic derivatives of erythromycin and of the propionic ester of erythromycin, mainly salts of erythromycin with acids containing sulfur atoms in their molecule. The exploitation of the therapeutical properties of thiolic compounds in combination with the properties of antibiotics has been already attemped. However (C.A. 93 38279 f) it was found that acetylcysteine and the derivatives thereof have an inhibiting action with respect to the activity of antibiotics. It has been now surprisingly found that the compounds of the present invention find therapeutical use in the cases in which erythromycin or the propionic ester thereof are already used and are generally characterized by a very low toxicity and by a high hematic concentration: these aspects are very important from the therapeutical point of view. The derivatives according to the present invention have the following general formula $$R-X \qquad (1)$$

wherein R is the radical of thenoyl alpha-mercaptopropionylglycine having the formula

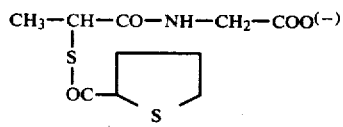

and X is the radical of erythromycin or of the propionyl ester of erythromycin having the formula

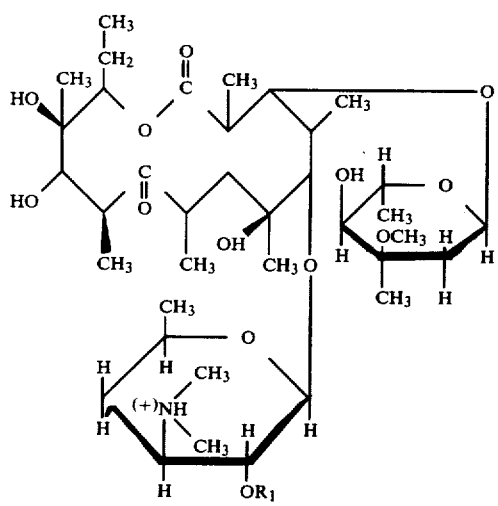

in which $R_1$ is H or $CH_3-CH_2-CO$

The compounds according to the invention are white, microcrystalline powders. Generally, the salt containing erythromycin monopropionyl ester is less soluble than the corresponding salt of erythromycin base; for both derivatives, moreover, the solubility increases in solvent mixtures, such as water-ethanol (1-5%), and water-ethylene glycol (1-5%). Their use is foreseen under all pharmaceutical forms: capsules, solutions, injectable preparations, aerosols, creams, powders and suspensions, both for human beings and for veterinary use. Particularly for the salt of erythromycin base there are foreseen pharmaceutical preparations of the injectable type or administerable by aerosol, whereas for the derivative of propionyl erythromycin there are preferred the orally administerable formulations and the suspensions. The two compounds are affected by sun light, humidity and heat, and are true salts, both from the chemical and from the physical point of view. The method for the preparation of the thiolic derivatives of erythromycin or of propionyl ester of erythromycin according to the present invention comprises reacting erythromycin base or the propionic ester of erythromycin with the acid, in a stoichiometrical ratio or in the presence of a slight excess of the antibiotic nucleous, and is characterized in that the reaction is carried out in an organic solvent, at a temperature of between 20° and 40° C. and in the presence of water in an amount not greater than 20%. In fact, it has been found, in a surprising manner, that the presence of water, preferably in an amount of 4-5% by volume with respect to the reaction solvent, permits the reaction to be completed with exceedingly good results. On the contrary, water amounts greater than 20% may cause the reaction product to be dissolved again in the aqueous/organic mixture.

The following examples, only given for illustrative purpose, disclose the preparation of the derivatives of the invention.

EXAMPLE 1

Erythromycin salt with theonyl alpha-mercapto-propionylglycine 88 g of erythromycin base are suspended in 700 mls of ligroin and, under stirring, 32.7 g of thenoyl mercaptopropionylglycine in 150 mls of 95% ethanol (the remaining being water) are added. The reaction mixture is heated to 40° C. maximum and the reaction mixture is converted to a product which after cooling, is filtered under reduced pressure. A white, crystalline product is obtained with a yield of 83% of the theoretical value and having melting point of between 130° and 137° C. The product is soluble in acetone, methanol, chloroform and ethyl acetate. The 2% water suspension has pH 7.9. The erythromycin titre on dry basis is 73.2% and the acid titre on dry basis is 26.8%. The FIG. 1 shows the IR spectrum of the resulting salt, wherein a band displacement from 1440 cm$^{-1}$ to 1420 cm$^{-1}$ between erythromycin and salt is seen.

EXAMPLE 2

Salt of erythromycin propionate with thenoyl alpha-mercapto-propionylglycine 126 g of erythromycin are suspended in 1400 mls of ligroin and, under stirring, 43.6 g of thenoyl alpha-mercaptopropionylglycine in 500 mls of 95% ethanol are added. The reaction mixture is heated to 40° C. maximum and, after conversion of the reaction mixture, the latter is cooled and filtered under reduced pressure. A white, crystalline product is obtained, having slightly bitter taste with a yield of 79-80% of the theoretical value. The melting point is 117°-125° C. (with decomposition). The product is soluble in acetone, methanol and ethyl acetate. It is poorly soluble in chloroform and almost insoluble in water. The titre of erythromycin propionate on dry basis is 74.6% and that of the acid on dry basis is 25.7%. The pH of the 2% water suspension is 5.6. FIG. 2 shows the IR spectrum, wherein, in comparison with the spectre of the starting substances, the disappearance of the band at 1210 cm$^{-1}$ and the displacement of bands from 1750 to 1630 cm$^{-1}$ and from 1440 to 1420 cm$^{-1}$ are observed. The compounds of the invention have been subjected to toxicological, pharmacological and pharmacodynamic tests aiming to assess the toxicity (and consequently the possibility of use in the therapeutical field) and the therapeutical properties. In the hereinafter stated results the compounds of the invention are indicated by the following abbreviations:

RV/06—erythromycin thenoyl-alpha-mercaptopropionylglycinate.

RV 16—erythromycin propionate thenoyl-alpha-mercaptopropionylglycinate.

(A) Acute toxicity

The acute toxicity was assessed in Swiss white mice by oral and intravenous route. The LD$_{50}$ values have been calculated by the methods of Probits, starting from the mortality recorded 10 days after the treatment.

| Compound | Administration route | LD$_{50}$ mg.kg (reliability limits) |
|---|---|---|
| erythromycin | os | >3000 |
| erythromycin hydrochloride | i.v. | 376.58 (478.78–296.20) |
| RV 06 | os | >3000 |
| RV 06 | i.v. | 426.43 (526.55–345.34) |
| RV 16 | os | >3000 |

(B) Antibacterial activity in vitro

The antibacterial activity in vitro of the compounds of the invention was assessed by comparing the different minimum inhibiting concentrations (MIC) with those of erythromycin base and of erythromycin estolate in Gram-positive and Gram-negative strains cultivated on Brain Heart Infusion (Difco). The tested samples of erythromycin estolate, RV 06 and RV 16 were previously hydrolized according to the prescription given in U.S. Pharmacopoea, XX edition, page 1347. In the following table I the MIC/ml values are indicated corresponding to the lowest concentration capable of inducing a complete inhibition of the bacterial development.

|  | STRAIN | erythromycin | erythromycin estolate | RV 06 | RV 16 |
|---|---|---|---|---|---|
| (1) | Staph. albus SS 03 | 0.05 | 0.05 | 0.5 | 0.05 |
| (2) | Staph. albus SS 04 | 0.05 | 0.05 | 0.025 | 0.05 |
| (3) | Staph. aureus SS 07 | 0.025 | 0.205 | 0.025 | 0.025 |
| (4) | Staph. aureus SS 08 | 0.025 | 0.025 | 0.025 | 0.025 |
| (5) | Staph. aureus SS 09 | 0.1 | 0.05 | 0.1 | 0.1 |
| (6) | Staph. aureus SS 10 | 0.1 | 0.2 | 0.1 | 0.05 |
| (7) | Strept. haemolyticus SS 17 | 3 | 3 | 3 | 1.5 |
| (8) | Strept. haemolyticus SS 18 | 1.5 | 3 | 1.5 | 1.5 |
| (9) | Strept. faecalis SS 19 | 0.1 | 0.1 | 0.1 | 0.1 |
| (10) | S. lutea ATCC 9341 | 0.01 | 0.01 | 0.01 | 0.01 |
| (11) | B. subtilis ATCC 6633 | 0.025 | 0.01 | 0.01 | 0.01 |
| (12) | B. subtilis SS 127 | 0.05 | 0.025 | 0.025 | 0.025 |
| (13) | B. cereus ATCC 11778 | 0.4 | 0.8 | 0.4 | 0.4 |
| (14) | B. anthranis SS 08 | 0.4 | 0.4 | 0.4 | 0.4 |
| (14bis) | B. anthranis SS 09 | 0.4 | 0.4 | 0.4 | 0.4 |
| (15) | Br. melitensis SS 19 | 3 | 3 | 3 | 3 |
| (16) | Br. abortus SS 7 | 12 | 6 | 6 | 12 |
| (17) | Citrobacter SS 05 | >200 | >200 | >200 | >200 |
| (18) | Citrobacter SS 09 | >200 | >200 | >200 | >200 |
| (19) | S. infantis SS 08 | 100 | 100 | 100 | 100 |
| (20) | S. heidelberg SS 18 | 100 | 100 | 100 | 100 |
| (21) | E. cloacae SS 07 | >200 | >200 | >200 | >200 |
| (22) | E. aerogenes SS 011 | 100 | 50 | 50 | 100 |
| (23) | Ps. aeruginosa SS 10 | 100 | 100 | 200 | 100 |
| (24) | Ps. aeruginosa SS 12 | >200 | 200 | 200 | 200 |
| (25) | E. coli SS 04 | 100 | 100 | 50 | 50 |
| (26) | E. coli SS 05 | 50 | 100 | 100 | 100 |
| (27) | E. coli SS 06 | 100 | 50 | 100 | 25 |
| (28) | E. coli SS 07 | 50 | 50 | 50 | 50 |
| (29) | Pr. mirabilis SS 09 | >200 | >200 | >200 | >200 |
| (30) | Pr. vulgaris SS 10 | >200 | >200 | >200 | >200 |
| (31) | Kl. aerogenes SS 71 | 50 | 100 | 100 | 100 |
| (32) | Kl. pneumoniae SS 04 | 100 | 100 | 100 | 100 |
| (33) | Sr. marcescens SS 03 | 200 | >200 | 200 | >200 |
| (34) | C. diphtheriae SS 19 | 0.01 | 0.025 | 0.02 | 0.02 |
| (35) | D. pneumoniae SS 23 | 0.05 | 0.05 | 0.05 | 0.05 |
| (36) | N. gonorreae SS 27 | 0.8 | 0.8 | 0.8 | 0.8 |
| (37) | N. meningitidis SS 04 | 0.8 | 1.5 | 0.8 | 0.8 |
| (38) | H. influentiae SS 02 | 1.5 | 1.5 | 0.8 | 1.5 |
| (39) | H. pertussis SS 03 | 0.4 | 0.4 | 0.4 | 0.2 |
| (40) | H. tubercolosis SS 03 | 50 | 50 | 50 | 50 |
| (41) | C. albicans SS 04 | 100 | 200 | 100 | 200 |
| (42) | Cl. tetani SS 17 | 0.4 | 0.2 | 0.2 | 0.8 |

(C) Antibacterial activity in vivo
Experimental infection induced by Staph. aureus and D. pneumoniae Swiss white mice of 20 g body weight were used, infected by parenteral administration of lethal amounts of pathogenic genes of Staph. aureus SS 07 and D. pneumoniae SS 23. The protecting activity expressed as $ED_{50}$ mg/kg was assessed for erythromycin base, erythromycin estolate, RV 06 and RV 16 administered by oral route as well as for erythromycin ethyl succinate and RV 06 administered by subcutaneous route. The antibiotics were administered at the time of injecting the infecting germ and 6 and 24 hours later. On the basis of the survival after 7 days, the $ED_{50}$ values were determined, as reported in the following table II and III, wherein the reliability limits are indicated in brackets.

TABLE II

Experimental infection by Staph. aureus SS 07
($ED_{50}$ mg/kg of erythromycin)

| Compound | Administration route | $ED_{50}$ mg/kg (reliability limits) |
|---|---|---|
| erythromycin ethyl succinate | s.c. | 1.03 (1.34–0.79) |
| RV 06 | s.c. | 1.13 (1.53–0.83) |
| erythromycin | os | 2.09 (2.36–1.86) |
| erythromycin estolate | os | 2.20 (2.44–1.99) |
| RV 06 | os | 2.02 (2.32–1.75) |
| RV 16 | os | 2.29 (2.58–2.04) |

TABLE III

Experimental infection by D. pneumoniae SS 23
($ED_{50}$ mg/kg of erythromycin)

| Compound | Administration route | $ED_{50}$ mg/kg (reliability limits) |
|---|---|---|
| erythromycin ethyl succinate | s.c. | 54.23 (69.76–42.16) |
| RV 06 | s.c. | 59.65 (75.02–47.43) |
| erythromycin | os | 113.53 (147.33–87.48) |
| erythromycin estolate | os | 127.89 (156.42–104.57) |
| RV 06 | os | 121.65 (150.91–98.06) |
| RV 16 | os | 113.88 (144.73–89.60) |

(D) Pharmacodynamics
(a) In the rat.

The absorption by oral route of the differents salts of erythromycin was investigated in Sprague-Dawley male rats which were administered, in groups of 6 animals fasted since 12 hours, with erythromycin, erythromycin estolate, RV 06 and RV 16 at the dose of 100 mg/kg (expressed as erythromycin) by oral route (gastric probing). The blood samples were taken 0.30, 1, 2, 3, 4, 5 and 6 hours after the administration. For the dosing the microbiological method, and as the test micro-organism, B subtilis were used. The experimental results are reported in the following table IV:

TABLE IV

Hematic levels in the rat (average plus standard error)

| Compound | N. of animals | 0.30 | 1 | 2 | 3 | 4 | 5 | 6 |
|---|---|---|---|---|---|---|---|---|
| erythromycin | 6 | 0.71 | 1.03 | 1.15 | 1.05 | 0.37 | 0.26 | 0.03 |
|  |  | 0.19 | 0.23 | 0.24 | 0.22 | 0.10 | 0.08 | — |
| erithromycin estolate | 6 | 0.68 | 1.74 | 2.49 | 1.49 | 0.61 | 0.37 | 0.04 |
|  |  | 0.07 | 0.14 | 0.35 | 0.22 | 0.10 | 0.05 | 0.01 |
| RV 06 | 6 | 0.37 | 0.80 | 1.23 | 0.80 | 0.60 | 0.33 | 0.07 |
|  |  | 0.10 | 0.19 | 0.36 | 0.21 | 0.17 | 0.11 | 0.03 |
| RV 16 | 6 | 0.73 | 1.97 | 2.82 | 1.28 | 0.58 | 0.35 | 0.05 |
|  |  | 0.09 | 0.09 | 0.14 | 0.11 | 0.08 | 0.05 | 0.01 |

(B) In the healthy volunteer

Group of 5 healthy volunteers, fasted since 24 hours, were administered by oral route with erythromycin estolate and RV 16 at a dose of 500 mg of erythromycin. The blood samples were taken 0.30, 1, 2, 3 and 4 hours after the administration. For the dosing, the microbiological method using a B. subtilis strain was adopted. The results are indicated in table V

TABLE V

Hematic levels in the healthy volunteer (average plus standard error)

| Compound | No. of animals | 0.30 | 1 | 2 | 3 | 4 | 5 | 6 |
|---|---|---|---|---|---|---|---|---|
| erithromycin estolate | 5 | 0.27 | 0.58 | 2.10 | 1.41 | 1.31 | — | — |
|  |  | 0.05 | 0.09 | 0.17 | 0.07 | 0.08 | — | — |
| RV 16 | 5 | 1.23 | 1.51 | 2.26 | 1.66 | 1.24 | — | — |
|  |  | 0.10 | 0.11 | 0.11 | 0.06 | 0.08 | — | — |

(E) Mucolytic activity

There was used the method described by Quevauviler et al. (Therapie 22, 485, 1967) according to which a bronchial hypersecretion is induced after exposure of the animal to an aerosol treatment with $SO_2$. The test was carried out on Sprague Dawley male rats. All rats were daily subjected to $SO_2$ inhalations, at a 0.03% concentration. After 50 hours of inhalation, the animals were divided in groups comprising 10 animals each. One group sa not treated (control animals), whereas the other animals were treated, two hours per day, for 15 days consecutively with inhalations of $SO_2$ and with erythromycin estolate and RV 16 by oral route at the dose of 500 mg/kg as well as with erythromycin ethyl succinate and RV 06 by intramuscular route at the dose of 250 mg/kg. The day after the last treatment, the anesthetized animals were sacrificed, and the lungs were removed and prepared for the microscopical and macroscopical examination. The results are indicated in the following Table VI.

TABLE VI

Qualitative and quantitative evaluation of the obstruction of the bronchial tract (% incidence)

| Treatment | administration route | Total obstruction | | | Partia ob-struction |
|---|---|---|---|---|---|
|  |  | compact plug | modular mass | pimply mass |  |
| $SO_2$ (control) | — | 40 | 13.33 | 6.66 | 26.66 |
| $SO_2$ + erythromycin estolate 500 mg/kg | oral | 46.66 | 20 | 6.66 | 20 |
| $SO_2$ + RV 16 500 mg/kg | oral | 26.66 | 6.66 | 6.66 | 6.66 |
| $SO_2$ + erythromycin ethyl succinate 250 mg/kg | i.m. | 53.33 | 26.66 | 13.33 | 20 |
| $SO_2$ + RV 06 250 mg/kg | i.m. | 25.66 | 6.66 | 6.66 | 13.33 |

Thereafter the histological examination of both control and treated animals was carried out.

(1) Control animals subjected to a $SO_2$ inhalation

The macroscopical bronchial obstructions as detected by the hystological examination correspond to a mucus mass admixed with fibrin and infiltrated with polynuclear elements. The hypersecretion does equally concern the peripheral bronchioles and the alveoles. As regards the bronchial epithelium there is revealed a proliferation of cup-shaped cells. The hyperplasy of the main bronchus appears as a stratification of 7 to 8 layers, associated to a bronchial hypertrophy.

(2) Animals treated with erythromycin estolate at the dose of 500 mg/kg by oral route and with erythromycin ethyl succinate at the dose of 250 mg/kg by intramuscular route From the histological examination it appears that the bronchial obstruction is formed by abundant mucus admixed with fibrin. Due to the irritating effect of $SO_2$, the bronchial epithelium reacts through a proliferation of cells, mainly cup-shaped cells. The hyperplasy is associated in a number of cases to a bronchial hypertrophy. In some cases, mucus secreting cells appear in the peripheral bronchioles.

(3) Animals treated with RV 16 at the dose of 500 mg/kg by oral route

In the animals having, under macroscopical examination, a free non obstructed bronchial tract, the histological examination revealed the presence of bronchi having almost normal appearance. An epithelial hyperplasy with a number of cup-shaped cells and reduced intrabronchial muco-purulents masses was detected. The hystological appearance of the obstructed bronchial tracts is fully like that of the control animals.

(4) Animals treated with RV 06 at the dose of 250 mg/kg by intramuscular route

The histological examination as carried out in the animals which under macroscopical examination had obstructed bronchi, revealed an appearance like that of the control animals.

Conclusions

From the toxicity tests it results that the erythromycin salts are devoid of toxicity when administered by oral route. When injected, they can be slightly toxic and have however $LD_{50}$ values comparable with that of erythromycin. From the tests of antibacterial activity in vitro it results that the erythromycin salts are active in a proportion like that of the erythromycin base. From the tests of antibacterial activity in vivo and from the pharmacodynamic tests it results that the compound RV 06 is poorly absorbed by oral route and in a route like that of erythromycin base. The propionic derivative RV 16 is absorbed by oral route in a rate practically analogous to that of erythromycin estolate. Contrarywise to erythromycin estolate, the drugs according to the invention are endowed with a good mucolytic activity which is revealed in the animals treated by $SO_2$ inhalation.

I claim:

1. Thiolic derivatives of erythromycin and of the propionic ester of erythromycin having the formula $$R-X \qquad (1)$$

wherein R is the radical of thenoyl alpha-mercaptopropionylglycine

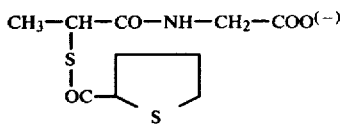

and X is the radical of erythromycin or of 3'-propionic ester of erythromycin having the formula

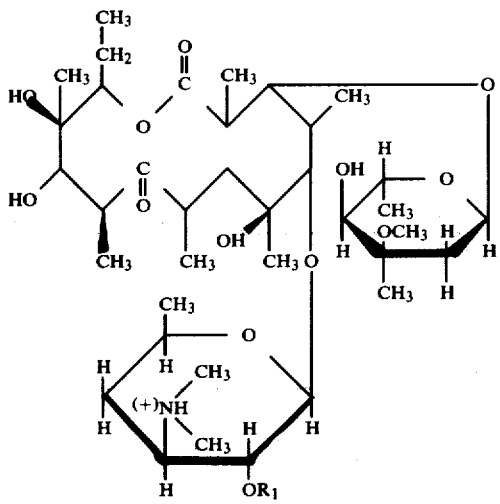

in which $R_1$ is H or $CH_3-CH_2-CO$.

2. The erythromycin salt of thenoyl alpha-mercaptopropionylglycine, according to claim 1.

3. The erythromycin 3'-propionic acid salt of propionic ester erythromycin with thenoyl alpha-mercaptopropionylglycine according to claim 1.

4. A pharmaceutical composition comprising as the active ingredient a thiolic derivative according to claim 1 in an amount effective to have an erythromycin activity together with a pharmaceutically acceptable carrier.

5. A pharmaceutical composition having antibacterial and mucolytic activity containing, as the active ingredient, a thiolic derivative according to claim 1 in an amount effective to have antibacterial and mucolytic activity together with a pharmaceutical acceptable carrier.

6. A pharmaceutical composition according to claim 5 in the form of a capsule or suspension suitable for oral administration.

7. A pharmaceutical composition according to claim 5 in a form suitable for administration by the parenteral route or as an aerosol.

* * * * *